US008864749B2

(12) United States Patent
Okada

(10) Patent No.: US 8,864,749 B2
(45) Date of Patent: Oct. 21, 2014

(54) SURGICAL INSTRUMENT

(75) Inventor: Yuta Okada, Hachioji (JP)

(73) Assignee: Olympus Corporation, Tokyo (JP)

( * ) Notice: Subject to any disclaimer, the term of this patent is extended or adjusted under 35 U.S.C. 154(b) by 873 days.

(21) Appl. No.: 12/603,004

(22) Filed: Oct. 21, 2009

(65) Prior Publication Data

US 2010/0042077 A1 Feb. 18, 2010

Related U.S. Application Data

(63) Continuation of application No. PCT/JP2008/059148, filed on May 19, 2008.

(30) Foreign Application Priority Data

May 22, 2007 (JP) .................................. 2007-135757

(51) Int. Cl.
*A61B 17/00* (2006.01)
*A61B 17/29* (2006.01)
*A61B 19/00* (2006.01)

(52) U.S. Cl.
CPC ......... *A61B 17/29* (2013.01); *A61B 2017/2905* (2013.01); *A61B 2019/266* (2013.01); *A61B 2017/2901* (2013.01); *A61B 2017/003* (2013.01); *A61B 19/26* (2013.01)

USPC ............................................................ 606/1

(58) Field of Classification Search
USPC ............................................................. 606/1
See application file for complete search history.

(56) References Cited

U.S. PATENT DOCUMENTS 5,624,380 A * 4/1997 Takayama et al. ............ 600/146
6,468,203 B2 * 10/2002 Belson .......................... 600/146

FOREIGN PATENT DOCUMENTS

| JP | 5-15914 | 3/1993 |
| JP | 5-57021 | 3/1993 |
| JP | 2578314 | 11/1996 |
| JP | 2002-524183 | 8/2002 |

* cited by examiner

*Primary Examiner* — Aaron Roane
(74) *Attorney, Agent, or Firm* — Scully, Scott, Murphy & Presser, P.C.

(57) ABSTRACT

A surgical instrument includes a surgical section that performs a predetermined procedure on a target organ in a body cavity, and an insertion section that includes an active movable section and a switchable tube section, the active movable section being provided with the surgical section at a top end of the active movable section, and the switchable tube section being selectively switchable between a pliable state and a rigid state.

5 Claims, 7 Drawing Sheets

SURGICAL INSTRUMENT

CROSS-REFERENCE TO RELATED APPLICATIONS

This is a Continuation Application of PCT Application No. PCT/JP2008/059148, filed May 19, 2008, which was published under PCT Article 21 (2) in Japanese.

This application is based upon and claims the benefit of priority from prior Japanese Patent Application No. 2007-135757, filed May 22, 2007, the entire contents of which are incorporated herein by reference.

BACKGROUND OF THE INVENTION

1. Field of the Invention

The present invention relates to a surgical instrument which is inserted into an organism to perform a procedure during a surgical operation.

2. Description of the Related Art

Recently, as minimally invasive procedures which do not require a large incision, endoscopic surgical operations have been carried out in a manner that various procedures are performed in a body cavity by incising an opening in a wall of a human body such as an abdominal wall and by further inserting an endoscope or a surgical instrument into the body cavity through the opening.

As surgical instruments used for such endoscopic surgical operations, there are rigid surgical instruments in which an insertion section to be inserted into a body cavity is formed of a rigid tube, as well as pliable surgical instruments in which the insertion section is formed of a pliable tube, for example, as disclosed in Patent Document 1. When performing a procedure at a deep part (such as a back side of an organ) in a body cavity, pliable surgical instruments are used in general because the posture of the insertion section can be adjusted vertically in accordance with that the insertion section moved along the organ in the body cavity or the operator's manipulation and the insertion section can therefore be inserted into the body cavity while changing bending of the insertion section.

Patent Document 1: Jpn. UM Appln. KOKOKU Publication No. 5-15914

BRIEF SUMMARY OF THE INVENTION

Accordingly, the present invention provides a surgical instrument which is flexibly configured and easily inserted into an organism, and does not move when performing a procedure.

According to one aspect of the invention, there is provided a surgical instrument comprising: a surgical section that performs a predetermined procedure on a target organ in a body cavity; and an insertion section that includes an active movable section and a switchable tube section, the active movable section being provided with the surgical section at a top end of the active movable section, and the switchable tube section being selectively switchable between a pliable state and a rigid state.

DETAILED DESCRIPTION OF THE INVENTION

Hereinafter, the best mode for carrying out the present invention will be described with reference to the drawings.

Figure 1A:
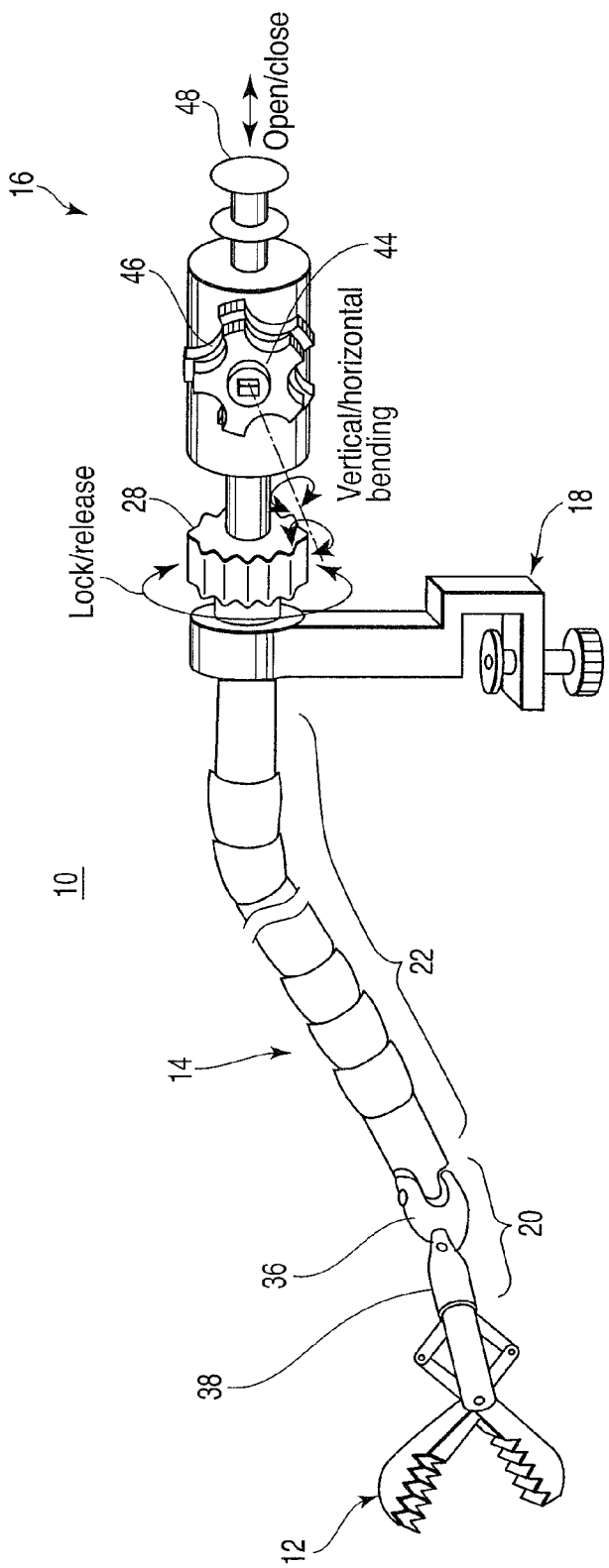
FIG. 1A is a view illustrating a structure of a surgical instrument according to an embodiment of the present invention.
Figure 1B:
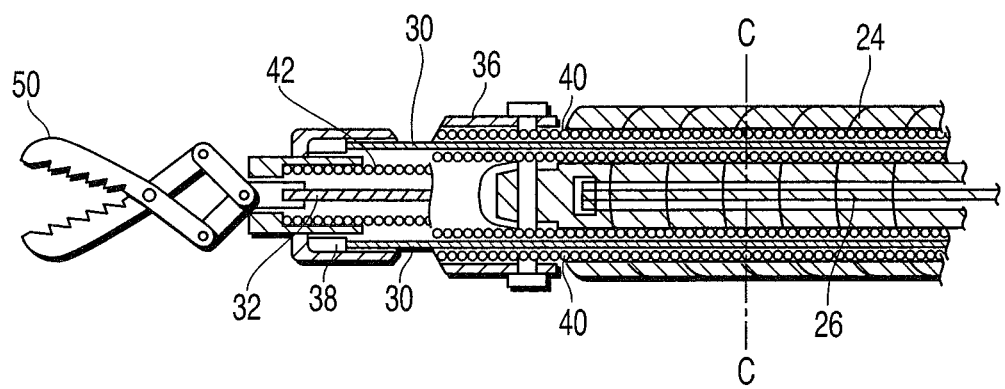
FIG. 1B is a view illustrating a cross-section of an insertion section of the surgical instrument according to the embodiment.
Figure 1C:
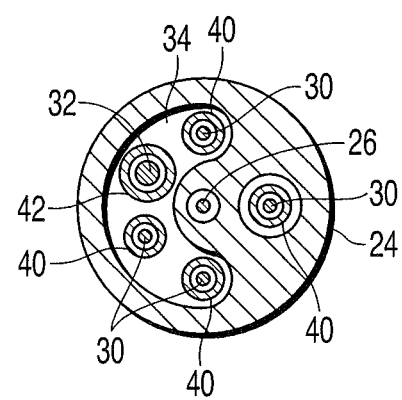
FIG. 1C is a sectional view along line C-C in FIG. 1B.

FIG. 1A is a view illustrating a structure of a surgical instrument 10 according to an embodiment of the present invention. FIG. 1B is a view illustrating a cross-section of an insertion section 14 of the surgical instrument 10. FIG. 1C is a cross-sectional view along line C-C in FIG. 1B.

The surgical instrument 10 according to the present embodiment is constituted by a surgical section 12, an insertion section 14, a manipulation section 16, and a fixing section 18. The surgical section 12 is a member (such as biopsy forceps) by which a predetermined procedure is performed on a target organ in a body cavity. The insertion section 14 is constituted by an active movable section 20 which is provided with the surgical section 12 at a top end of the active movable section 20, and a switchable tube section 22 which can be selectively switched between a pliable state and a rigid state. The manipulation section 16 is formed at a position where the manipulation section 16 is situated outside a human body when performing the predetermined procedure, as a member for manipulating the surgical section 12. The fixing section 18 is a member for fixing the surgical instrument 10 to an operating table, etc.

The switchable tube section 22 is constructed by arranging a large number of switchable tubes 24 so as to be continuously in contact with each other. The switchable tubes 24 have a function as joints. A joint-lock wire 26 communicates through the inside of the switchable tubes 24. One end of the joint-lock wire 26 is fixed to the switchable tubes 24 which is arranged at a distal end. The other end of the joint-lock wire 26 is wound about a pivot member (not illustrated) which pivots in accordance with rotation of a dial 28 provided on the manipulation section 16. Tension of the joint-lock wire 26 can be adjusted by manipulating the dial 28. That is, when the dial 28 is rotated to a lock release position, the tension of the joint-lock wire 26 is then eased, so that contact force between the switchable tubes 24 is eased. Accordingly, the switchable tube section 22 of the insertion section 14 are set in a pliable state, thereby allowing joints to freely move into various bent states. In contrast, when the dial 28 is rotated to a lock fix position, the tension of the joint-lock wire 26 is then increased, so that the contact force between the switchable tubes 24 is increased. Accordingly, the switchable tube section 22 of the insertion section 14 are set in a rigid state. That is, the joints are locked, thereby maintaining a bent state into which the joints have been configured in the pliable state.

Also inside the switchable tubes 24, a further four bending wires 30 and one top open/close wire 32 are provided communicating through the switchable tubes 24. In this case, a communicating hole 34 having a semi-circular arcuate cross-section is formed in each of the switchable tubes 24, as illustrated in FIG. 1C, so that the insertion section 14 may be configured into any bent state. Through inside of the communicating holes 34, the three of the four bending wires 30 and top open/close wire 32 are extended. The bending wires 30 and the top open/close wire 32 are respectively provided with coils 40 and a coil 42, which are wound about the wires 30 and the wire 32. The coils 40 and 42 are bendable and therefore can be bent into the same shape as the active movable section 20 even if the active movable section 20 is bent. Thus, since the wires 30 and 32 are included in the coils 40 and 42, parts of the wires 30 and 32 which are included in the coils 40 and 42 are not influenced from any bent shape into which the active movable section 20 can be bent. Accordingly, the active movable section 20 can freely configure its own bent state.

The active movable section 20 described above is constituted by: a first movable section 36 which is attached to the one of the switchable tubes 24 arranged at the distal end of the switchable tube section 22 of the insertion section 14 in a manner that the first movable section 36 can swing in directions horizontal to the switchable tube 24; and a second movable section 38 which is attached to the first movable section 36 in a manner that the second movable section 38 can swing in directions vertical to the first movable section 36. Inside the first movable section 36, the one top open/close wire 32 and the four bending wires 30 are provided. Inside the second movable section 38, the one top open/close wire 32 and two of the four bending wires 30, which contribute to movement of the second movable section 36, are provided.

Opposed two (omitted from FIG. 1B) of the four bending wires 30 provided in the first movable section 36 contribute to swinging of the first movable section 36 in the horizontal directions. These opposed two bending wires 30 are each fixed, at one end of these opposed two bending wires 30, to the first movable section 36, and are each wound, at the other end of these opposed two bending wires 30, about a pivot member (not illustrated) which pivots in accordance with rotation of the dial 44 provided at the manipulation section 16 described above. Accordingly, tension of these opposed two bending wires 30 can be adjusted by manipulating the dial 44. The coils 40 surrounding the foregoing opposed two bending wires 30 are fixed to the one of the switchable tubes 24 arranged at the distal end. When the bending wires 30 are pulled by rotating the dial 44, the first movable section 36 moves horizontally. Further, as illustrated in FIG. 1B, the other opposed two bending wires 30 contribute to swinging of the second movable section 38 in the vertical directions. These opposed two bending wires 30 are each fixed, at one end of these opposed two bending wires 30, to the second movable section 38, and are each wound, at the other end of these opposed two bending wires 30, about a pivot member (not illustrated) which pivots in accordance with rotation of a dial 46 provided at the manipulation section 16. Accordingly, tension can be adjusted by manipulating the dial 46. The coils 40 surrounding these opposed two bending wires 30 are fixed to the first movable section 36. The second movable section 38 moves vertically when these bending wires 30 are pulled, as in the movable section 36.

An end of the top open/close wire 32 is connected to a rear end of the surgical section 12, and the other end thereof is connected to a slider 48 provided on the manipulation section 16. By pulling/pushing the slider 48, a surgical section top end 50 can be opened/closed. The coil 42 surrounding the top open/close wire 32 is fixed to a position closer to the top end than the second movable section 38.

Figure 2:
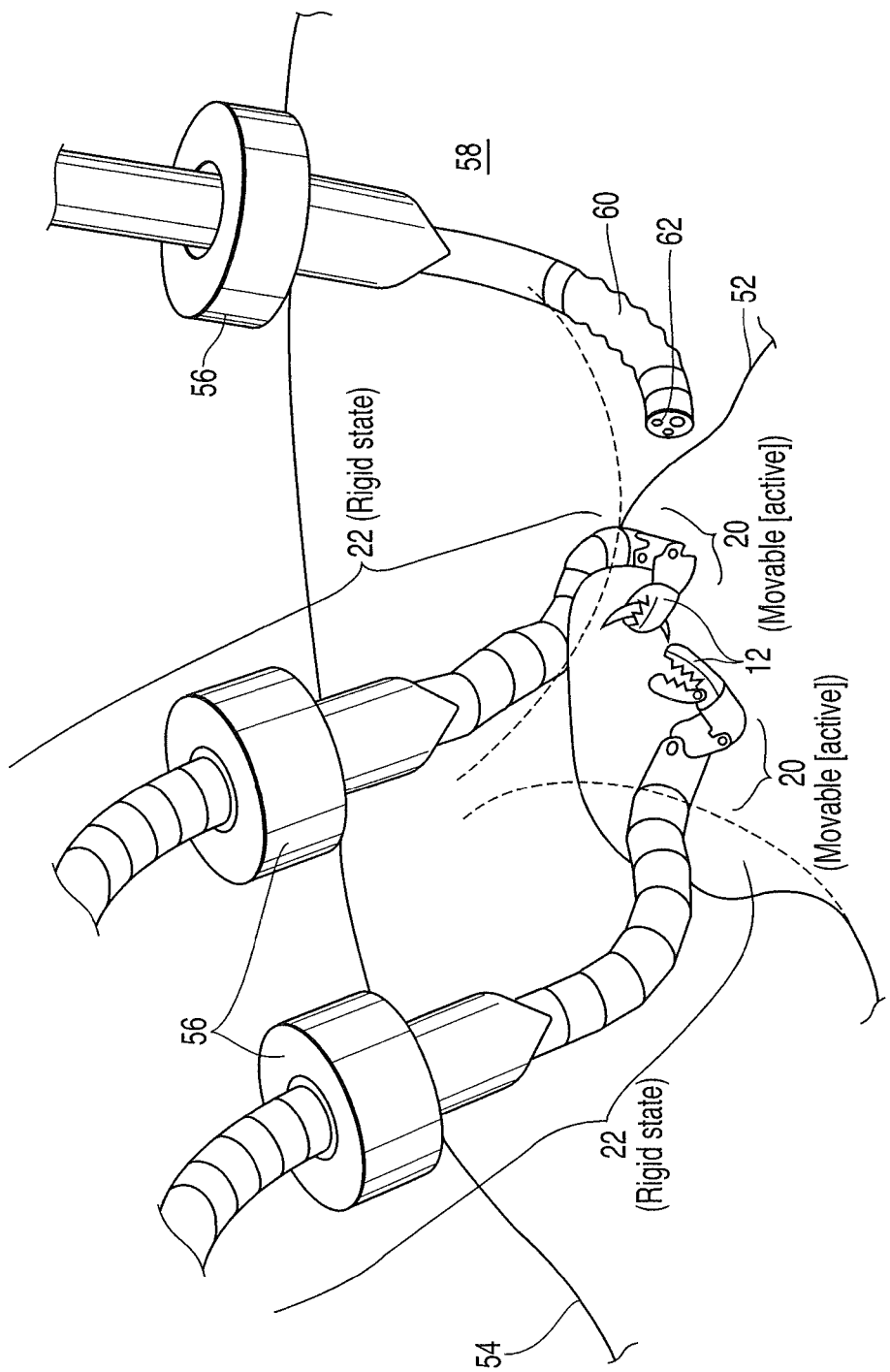
FIG. 2 is a view illustrating a use state of the surgical instrument according to the embodiment.

FIG. 2 is a view illustrating a use state of the surgical instrument 10 according to the present embodiment.

Specifically, in the case of treating a surgery target portion of a target organ 52 by use of the surgical instrument 10 according to the present embodiment, the surgical instrument 10 is inserted into a body cavity 58 through a trocar 56 inserted in and fixed to an opening incised in a body wall 54, with the switchable tube section 22 of the insertion section 14 set in a pliable state (a lock released state). While monitoring with a camera 62 provided at a top end of an endoscope 60 inserted through another trocar 56, the surgical section 12 is set at the surgery target portion of the target organ 52. Thereafter, the switchable tube section 22 of the surgical section 12 is set in a rigid state (locked). The position of the switchable tube section 22 set in the rigid state is thereby fixed.

As has been described above, when inserted into an organism, the switchable tube section 22 is set in a pliable state, so that the insertion section 14 can be easily inserted into the organism. When the insertion section which is entirely set in the pliable state is used, the bottom end side of the insertion section moves in accordance with the operator's manipulation. As a result, there is a difficulty in manipulating the insertion section (surgical section) into a position or a posture as desired (required) by the operator. However, if the active movable section 20 and the switchable tube section 22 are provided in the insertion section 14 and the switchable tube section 22 is set in the rigid state when performing a procedure, as in the present embodiment, the surgical section 12 does not unintentionally move during the procedure. Also in the case of using an insertion section which is entirely set in a rigid state, there is a difficulty in manipulating the insertion section into a position or a posture as desired (required) by the operator. However, according to the present embodiment, even when the switchable tube section 22 is set in the rigid state, the active movable section 20 can freely change a position and a posture of the surgical section 12 as coordinates based on the attachment section for the switchable tube section 22 as a reference because the active movable section 20 is provided. Accordingly, manipulation ability of the surgical section 12 improves. Further, a surgery target portion can be moved, for example, by adjusting a direction of the active movable section 20, with the surgery target portion of the target organ 52 grasped by the surgical section 12.

Further, a method for inserting the surgical instrument 10 according to the present embodiment into the body cavity 58 will now be described with reference to FIGS. 3A to 3D.

Figure 3A:
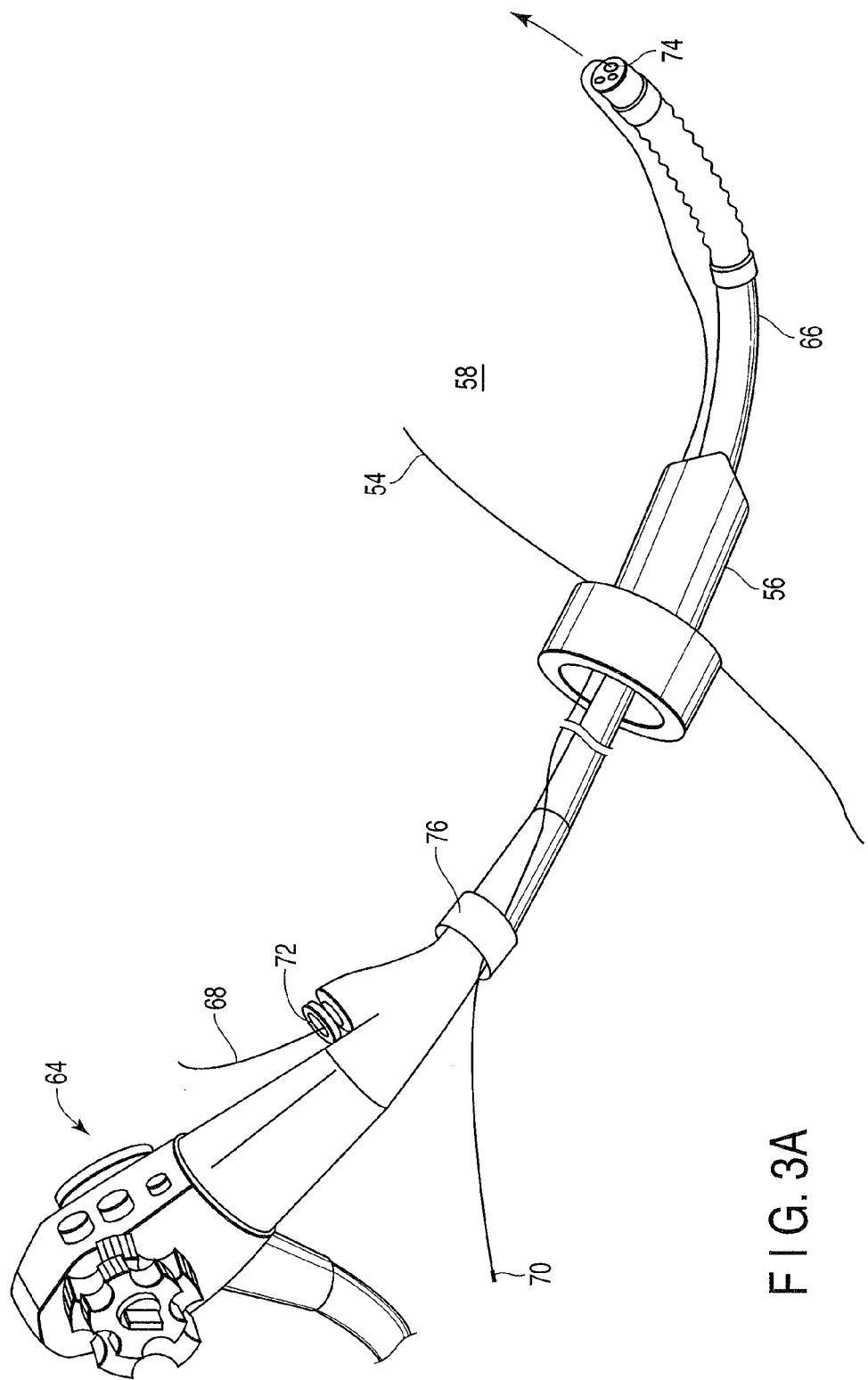
FIG. 3A is a view for describing an insertion method for inserting the surgical instrument according to the embodiment into a body cavity.
Figure 3B:
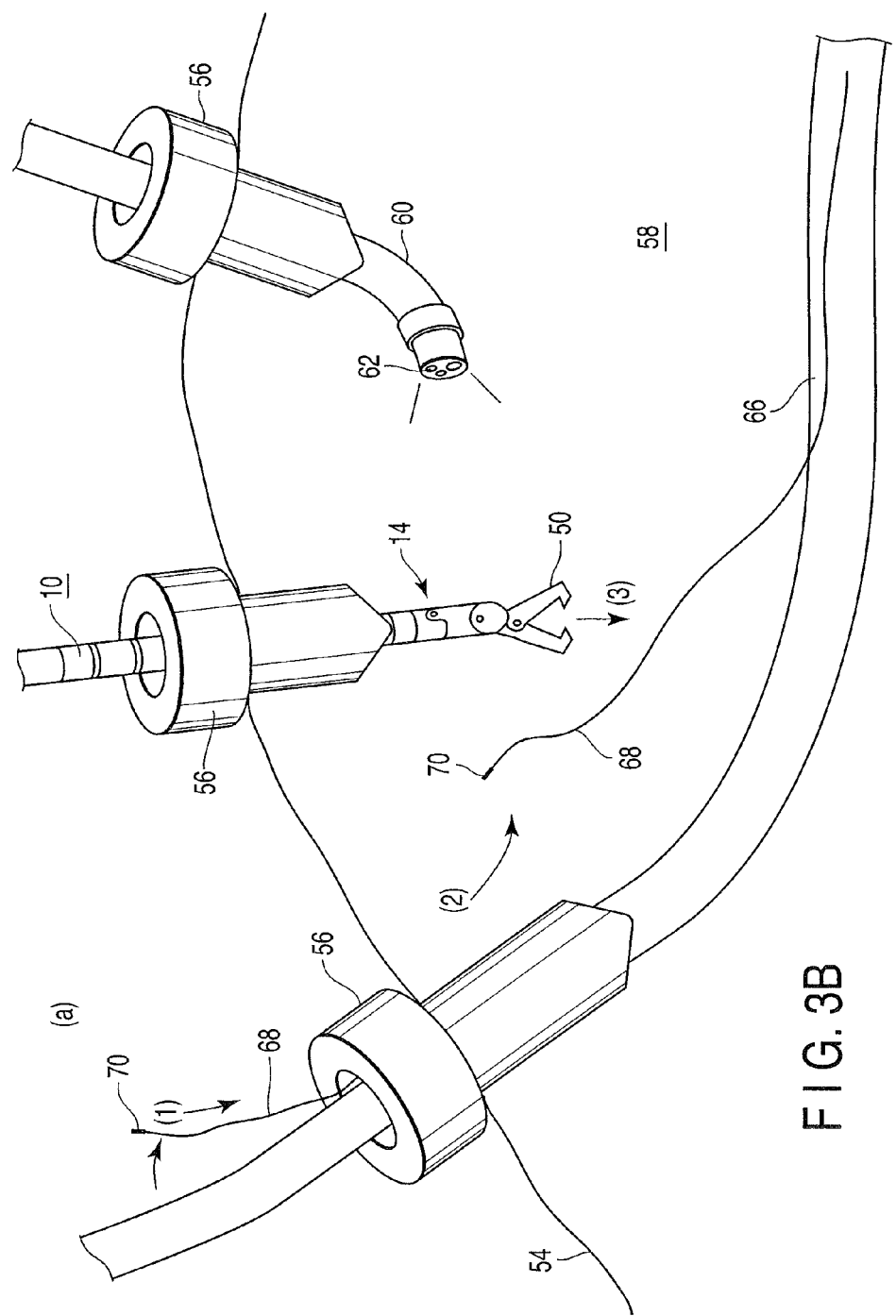
FIG. 3B is also a view for describing the insertion method for inserting the surgical instrument according to the embodiment into a body cavity.
Figure 3C:
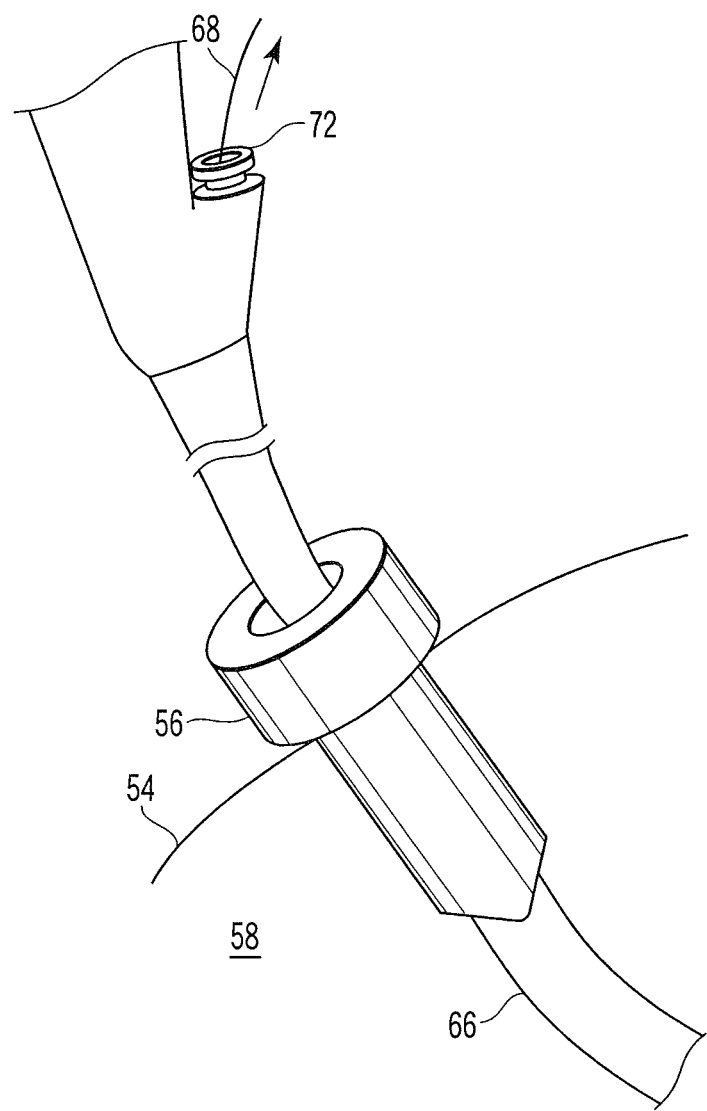
FIG. 3C is also a view for describing the insertion method for inserting the surgical instrument according to the embodiment into a body cavity.
Figure 3D:
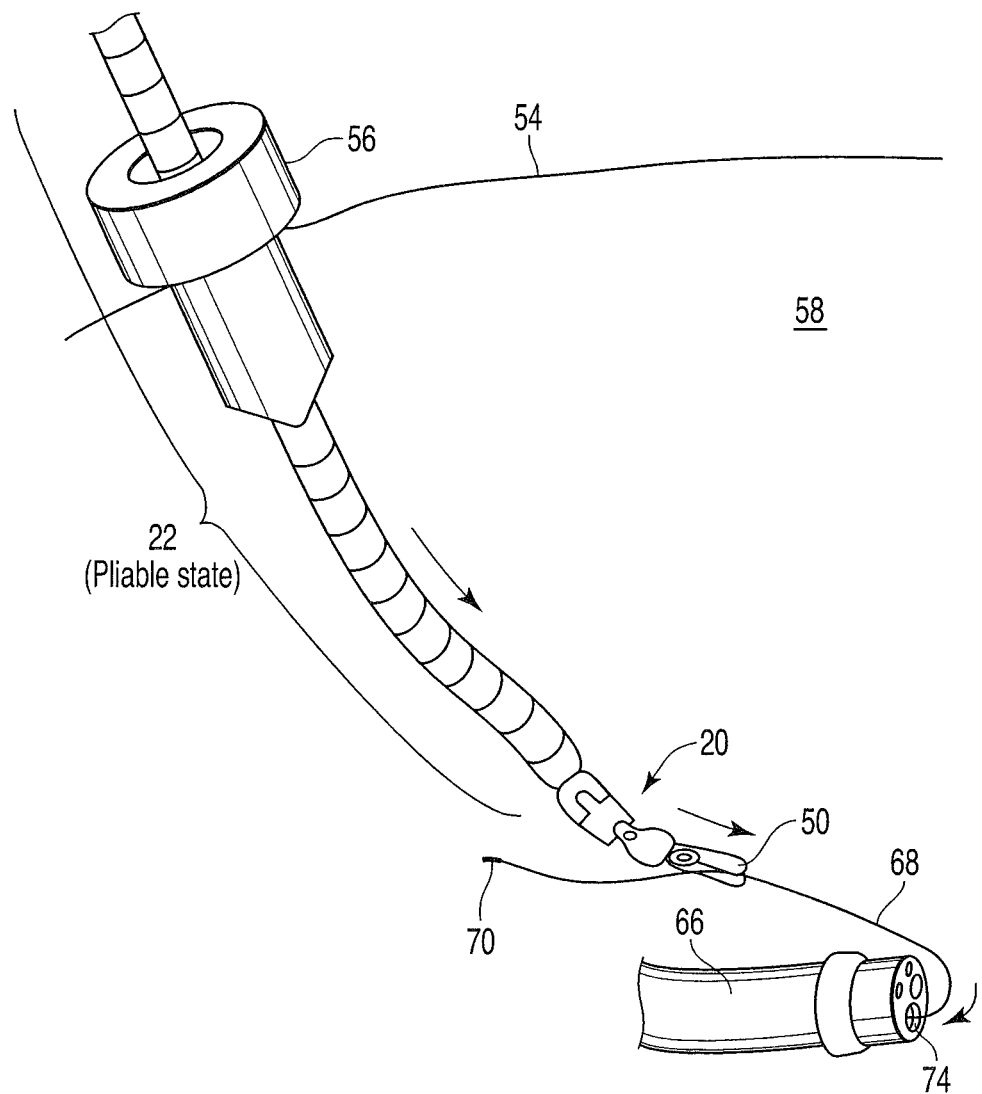
FIG. 3D is also a view for describing the insertion method for inserting the surgical instrument according to the embodiment into a body cavity.

Specifically, as illustrated in FIG. 3A, another endoscope 64 than the endoscope 60 is used. In an endoscope insertion section 66 of the endoscope 64, a forceps channel for inserting biopsy forceps is provided, communicating between a top end of the endoscope insertion section 66 and a part which is situated outside a human body when the endoscope insertion section 66 is inserted in the body cavity 58. Further, a front end 70 of a guide wire 68 is inserted from an inlet port 72 of the forceps channel, extends through the forceps channel in the endoscope insertion section 66, and extends out of an outlet port 74 at a top end. The front end 70 is returned along outside of the endoscope insertion section 66 to a temporary fixing section 76 near the inlet port 72, and is fixed with a tape. After the guide wire 68 is prepared in this manner, a still another trocar 56 other than trocars 56 for inserting the surgical instrument 10 and the endoscope 60 is inserted in and fixed to an opening incised in a body wall 54. The endoscope 64 is inserted into the body cavity 58 through the still another trocar 56.

Further, when the endoscope insertion section 66 is inserted to situate the temporary fixing section 76 near the still another trocar 56, the guide wire 68 is then released from temporary fixation using a tape described above, as denoted by an arrow (1) in FIG. 3B, and the endoscope insertion section 66 is further inserted. As a result, as denoted by an arrow (2) in FIG. 3B, the front end 70 of the guide wire 68 is dropped into the body cavity 58 from the still another trocar 56. Further, the insertion section 14 of the surgical instrument 10 according to the present embodiment is inserted into the body cavity 58 through the still another trocar 56 (wherein the switchable tube section 22 may be in either the pliable or rigid state at this time). While monitoring through the camera 62, the guide wire 68 is grasped, at the front end 70 thereof, with a surgical section top end 50 of the surgical section 12 provided at a top end of the insertion section 14, as denoted by an arrow (3) in FIG. 3B.

With the guide wire 68 grasped in this manner by the surgical section 12, the endoscope 66 is further inserted while monitoring through the camera 62 of the endoscope 60. The top end of the endoscope 66 is accordingly moved to the surgery target portion of the target organ 52. When the top end is moved to the position of the surgery target portion, the switchable tube section 22 is switched to the pliable state, and the guide wire 68 is pulled from a side of the inlet port 72 of the forceps channel 72, as denoted by an arrow in FIG. 3C. Then, as denoted by an arrow in FIG. 3D, the surgical section 12 of the surgical instrument 10 which grasps the guide wire 68 near the front end 70 thereof is pulled in accordance with movement of the guide wire 68, and moves to vicinity of the outlet port 74 of the forceps channel at the top end of the endoscope insertion section 66, that is vicinity of the surgery target portion of the target organ 52. This state is monitored through the camera 62 of the endoscope 60. When the surgical section 12 of the surgical instrument 10 reaches a desired position, the switchable tube section 22 is switched to the rigid state, and the surgical section top end 50 is set in an open state, to release the grasp of the guide wire 68. The guide wire 68 is still further pulled to come out of the forceps channel of the endoscope 64. The endoscope 64 may be pulled out in a similar manner, or the position of the endoscope 64 may be further adjusted and used for monitoring a procedure or an operative field.

As has been described above, the surgical instrument 10 according to the present embodiment includes: the active movable section 20 as an active movable section which can be manipulated from outside of a human body by an operator; and the switchable tube section 22 as a passive movable section which can be selectively switched between pliable and rigid states. The surgical instrument 10 can therefore be flexibly configured and easily inserted into an organism, and can be configured to be immovable during a procedure.

The present invention has been described above on the basis of an embodiment. However, the invention is not limited to the embodiment described above but may of course be variously modified or practically applied within the scope of the invention.

Additional Notes

Inventions as configured below can be extracted from the specific embodiments described above.

(1) A surgical instrument comprising:
a surgical section that performs a predetermined procedure on a target organ in a body cavity; and
an insertion section that includes an active movable section and a switchable tube section, the active movable section being provided with the surgical section at a top end of the active movable section, and the switchable tube section being selectively switchable between a pliable state and a rigid state.

Correspondence to Embodiment

The body cavity 58 in the embodiment corresponds to the body cavity described above, the target organ 52 corresponds to the target organ described above, the surgical section 12 corresponds to the surgical section described above, the active movable section 20 corresponds to the active movable section described above, the switchable tube section 22 corresponds to the switchable tube section described above, the insertion section 14 corresponds to the insertion section described above, as well as the surgical instrument 10 corresponds to the surgical instrument described above.

Operation and Effects

The surgical instrument described in (1) includes the active movable section, which is provided with the surgical section formed at a top end and is always pliable, and the switchable tube section which can become either pliable or rigid. Therefore, the surgical instrument can be flexibly configured and easily inserted into an organism, and becomes immovable during a procedure.

(2) The surgical instrument according to (1), wherein the switchable tube section of the insertion section is set in the pliable state when inserted into body cavity, and is set in the rigid state when the performing the predetermined procedure on the organ in the body cavity.

Operation and Effects

According to the surgical instrument described in (2), the switchable tube section of the insertion section is set in a pliable state when being inserted into a body cavity, and is set in a rigid state when performing a predetermined procedure on an organ in the body cavity. Therefore, a procedure is facilitated even at other portions than a surgery target portion which is very close to an insertion opening extending to the body cavity.

(3) The surgical instrument according to (1), further comprising a manipulation section that is formed, to manipulate the surgical section, at a position where the manipulation section is situated outside a human body when performing the predetermined procedure, wherein
the manipulation section includes a selection section by which switching is made to select the pliable state or the rigid state for the switchable tube section of the insertion section.

Correspondence to Embodiment

The manipulation section 16 in the embodiment corresponds to the manipulation section described above, as well as the dial 28 corresponds to the selection section.

Operation and Effects

According to the surgical instrument described in (3), the selection section for switching is outside a human body, and therefore, manipulation ability is excellent.

(4) The surgical instrument according to (1), wherein the manipulation section further includes a posture manipulation section by which the posture of the active movable section is manipulated.

Correspondence to Embodiment

The dials 44 and 46 in the embodiment correspond to the posture manipulation section.

Operation and Effects

According to the surgical instrument described in (4), the posture of the active movable section can be freely adjusted to set the surgical section at a surgery target portion of a target organ.

What is claimed is:
1. A surgical instrument comprising:
a surgical section that performs a predetermined procedure on a target organ in a body cavity;
an insertion section that includes an active movable section and a switchable tube section, the active movable section being provided with the surgical section at a top end of the active movable section, and the switchable tube section being selectively switchable between a pliable state and a rigid state; and a joint-lock wire which is configured to switch the switchable tube section to one of the pliable state and the rigid state, wherein the joint-lock wire communicates through an inside of the switchable tube section, one end of the joint-lock wire is fixed to a distal end of the switchable tube section, another end of the joint-lock wire is wound about a pivot member, and the pivot member pivots in accordance with rotation of a dial configured to adjust tension of the joint-lock wire.

2. The surgical instrument according to claim 1, wherein the switchable tube section of the insertion section is set in the pliable state when inserted into body cavity, and is set in the rigid state when the performing the predetermined procedure on the organ in the body cavity.

3. The surgical instrument according to claim 1, further comprising a manipulation section that is formed, to manipulate the surgical section, at a position where the manipulation section is situated outside a human body when performing the predetermined procedure, wherein the manipulation section includes a selection section by which switching is made to select the pliable state or the rigid state for the switchable tube section of the insertion section.

4. The surgical instrument according to claim 3, wherein the manipulation section further includes a posture manipulation section by which the posture of the active movable section is manipulated.

5. The surgical instrument according to claim 1, further comprising:

at least one bending wire communicating through the inside of the switchable tube section for bending the active movable section, wherein the bending wire is provided with a coil inside the switchable tube section, the coil being wound about the wire.

* * * * *